United States Patent [19]

Takano et al.

[11] Patent Number: 5,484,689
[45] Date of Patent: Jan. 16, 1996

[54] OPTICAL RECORDING MATERIAL COMPRISING A BIS-DITHIOBENZILNICKEL COMPLEX

[75] Inventors: Toshiyuki Takano; Toshimi Satake, both of Tokyo, Japan

[73] Assignee: Nippon Paper Industries Co., Ltd., Tokyo, Japan

[21] Appl. No.: 171,857

[22] Filed: Dec. 22, 1993

Related U.S. Application Data

[62] Division of Ser. No. 40,452, Apr. 1, 1993, abandoned.

[30] Foreign Application Priority Data

Apr. 2, 1992 [JP] Japan ................................ 4-080646

[51] Int. Cl.$^6$ ................................................. G03C 1/735
[52] U.S. Cl. ...................... 430/341; 430/338; 430/944; 430/945
[58] Field of Search ................................. 430/338, 341, 430/944, 945; 503/211

[56] References Cited

U.S. PATENT DOCUMENTS

| 4,529,684 | 7/1985 | Sasagawa et al. | 430/269 |
|---|---|---|---|
| 4,783,393 | 11/1988 | Brazas, Jr. et al. | 430/270 |
| 4,806,664 | 2/1989 | Schrott et al. | 556/136 |
| 4,921,317 | 5/1990 | Suzuki et al. | 350/311 |
| 5,100,711 | 3/1992 | Satake et al. | 428/64 |
| 5,178,990 | 1/1993 | Satake et al. | 430/346 |
| 5,182,409 | 1/1993 | Takuma et al. | 556/146 |
| 5,234,797 | 8/1993 | Satake et al. | 430/338 |

FOREIGN PATENT DOCUMENTS

| 9012019 | 10/1990 | WIPO | 556/146 |
|---|---|---|---|

OTHER PUBLICATIONS

Schrauzer and V. P. Mayweg, "Preparation, Reactions, and Structure of Bisdithio . . . ", Dec. 3, 1964, pp. 1483–1489.
Schrauzer, et al., Angew. Chem. internat. Edit. vol. 3 (1964), No. 5.
JP 3-197084 (abstract) "Optical Data Recording Medium", Dainippon Printing Co., Ltd., Aug. 28, 1991.
JP-2-120082 (abstract) "Optical Recording Material", Jujo Paper Co., Ltd., May 8, 1990.
JP-63-227597 (abstract) "Bis(Dithiobenzyly)Nickel Complex Compound", Midori Kagakuy K.K., Sep. 21, 1988.
JP-1-61492 (abstract) "Bis(Dithiobenzyl) Complex Compound", Midori Kagaku K.K., Mar. 8, 1989.
JP-3-148290 (abstract) "Ditquikebe-Type Organic Metal Complex, Its Production, Thin Film and Production Thereof", Jun. 25, 1991.
Mueller–Westerhoff, et al., "The Synthesis of Dithiolene Dyes With Strong Near–IR Absorption", Aug. 10, 1990, pp. 909–932.

*Primary Examiner*—Charles L. Bowers, Jr.
*Assistant Examiner*—John A. McPherson
*Attorney, Agent, or Firm*—Sherman and Shalloway

[57] ABSTRACT

A benzoin compound is synthesized from phenylglyoxal and a substituted benzene derivative, and the resulting benzoin compound is converted to a bis-dithiobenzilnickel complex using phosphorus pentasulfide/nickel chloride. The bis-dithiobenzilnickel complex is useful as a near-infrared absorbing material to be coated on paper, and the benzoin compound is useful as an intermediate of the complex. The obtained bis-dithiobenzilnickel complex can be applied to an optical recording material, a near-infrared absorbing resin, a near-infrared absorbing hard coating agent and a near-infrared absorbing glass composite.

9 Claims, 1 Drawing Sheet

OPTICAL RECORDING MATERIAL COMPRISING A BIS-DITHIOBENZILNICKEL COMPLEX

This application is a division of application Ser. No. 08/040,452, filed Apr. 1, 1993 now abandoned.

BACKGROUND OF THE INVENTION

1. Field of the Invention

This invention relates to novel bis-dithiobenzilnickel complexes which are used as near-infrared absorbing materials and to novel benzoin derivatives which are useful as intermediates of the complexes.

2. Description of the Prior Art

Bis-dithiobenzilnickel complexes such as bis-dithiobenzilnickel, bis-(4-dimethylamino)-dithiobenzilnickel, and bis-(4-diethylamino)-dithiobenzilnickel have strong absorption in the near-infrared region of 700–1,300 nm, and thus are known to be used as near-infrared absorbing materials or organic materials for optical disks, as reported, for example, in Senryo To Yakuhin (Dyes and Chemicals), 35 5 (1990) [4-25], Japanese Patent Laid-open Publication 63-227597, and Japanese Patent Laid-open Publication 64-61432.

On the other hand, an optical recording medium comprising a near-infrared absorbing material and a thermal recording material is disclosed in Japanese Patent Laid-open Publication 2-120082. However, these complexes show dark green colors. Since optical recording materials based on paper using these complexes are required to have high brightness, complexes of paler in color have been in demand. Furthermore, since the maximum absorptions of these complexes differ between in a solid state and in solution, especially when coated on paper, the maximum absorptions are shifted from those of the solution. Therefore, when these complexes are applied to an optical recording material using a semiconductor laser (wavelength: 830 nm), it is necessary to use one which has a maximum absorption in the vicinity of 830 nm in a solid state. However, the known bis-dithiobenzilnickel complexes do not have suitable maximum absorptions near 830 nm, for example, bis-dithiobenzilnickel has its maximum absorption in 850–870 nm, bis-(4-dimethylamino)-dithiobenzilnickel has a maximum absorption in 1,060–1,070 nm, and bis-(4-diethylamino)-dithiobenzilnickel has a maximum absorption in 1,100–1,120 nm.

DETAILED DESCRIPTION OF THE INVENTION

In the present invention, in order to solve the above problems, novel bis-dithiobenzil compounds are synthesized.

In accordance with the present invention, there are provided, as a first embodiment, novel bis-dithiobenzilnickel complexes of Formula [1] and/or [2]:

(wherein $R_1$ to $R_5$ are the same or different, and denote substituted or unsubstituted alkyl, cycloalkyl, alkoxy, aryl, aryloxy, halogen atom, or hydrogen atom, except for substituted or unsubstituted amino group and alkoxyalkoxy group. However, a case where all of $R_1$ to $R_5$ are hydrogen atoms is excepted.)

There are two possibilities of the structure of the complexes of present invention, Formulas [1] and [2]. The complex of the present invention is one of them or mixtures thereof.

The bis-dithiobenzilnickel complexes of Formula [1] and/or [2] include, for example, Structural formulas of the complexes are shown only for the type of Formula [1], but the complexes of the present invention also includes those of the type of Formula [2].

Bis-(4-methyldithiobenzil)-nickel [21]
Bis-(4-ethyldithiobenzil)-nickel [22]
Bis-(4-n-propyldithiobenzil)-nickel [23]
Bis-(4-iso-propyldithiobenzil)-nickel [24]
Bis-(4-n-butyldithiobenzil)-nickel [25]
Bis-(4-sec-butyldithiobenzil)-nickel [26]
Bis-(4-tert-butyldithiobenzil)-nickel [27]
Bis-(4-n-amyldithiobenzil)-nickel [28]
Bis-(4-n-hexyldithiobenzil)-nickel [29]
Bis-(4-n-heptyldithiobenzil)-nickel [30]
Bis-(4-n-octyldithiobenzil)-nickel [31]
Bis-(2,5-dimethyldithiobenzil)-nickel [32]
Bis-(3,5-dimethyldithiobenzil)-nickel [33]
Bis-(3,4-dimethyldithiobenzil)-nickel [34]
Bis-(2,4,6-trimethyldithiobenzil)-nickel [35]
Bis-(2,3,4,5-tetramethyldithiobenzil)-nickel [36]
Bis-(4-methoxydithiobenzil)-nickel [37]
Bis-(2,5-dimethoxydithiobenzil)-nickel [38]

Bis-(4-phenyldithiobenzil)-nickel [39]
Bis-(4-phenoxydithiobenzil)-nickel [40]
Bis-(4-cyclohexyldithiobenzil)-nickel [41]
Bis-(4-chlorodithiobenzil)-nickel [42]

-continued

-continued

The bis-dithiobenzilnickel complexes can be synthesized by a method of G. N. Schrauzer, et al. in which the corresponding benzoin derivative is treated with phosphorus pentasulfide/nickel chloride [JOURNAL OF THE AMERICAN CHEMICAL SOCIETY, 87, (1965), 1483–1489]. Specifically, the benzoin derivative is dissolved in 1,4-dioxane, phosphorus pentasulfide is added, and reacted under reflux. The reaction mixture is filtered, aqueous nickel chloride solution is added to the filtrate, and refluxed again. The resulting precipitate is filtered and purified to yield bis-dithiobenzilnickel complex of Formula [1] and/or [2].

Since the substituent groups of the bis-dithiobenzilnickel complex are derived from that of benzoin derivative, the synthesis of benzoin derivative is important in the synthesis of the complex.

The most general method of obtaining the benzoin derivative is the reaction called "benzoin condensation."

For example, Japanese Patent Laid-open Publication 63-227597, Japanese Patent Laid-open Publication 3-148290, and the like describe examples in which a benzoin derivative is synthesized by the use of the benzoin condensation, and then a bis-dithiobenzilnickel complex is synthesized. The benzoin condensation is a method in which two molecules of benzaldehyde derivative are reacted in the presence of cyan ions. Therefore, this method is normally suitable for symmetrically introducing substituent groups into both aromatic rings of benzoin.

2X-Ph-CHO→X-Ph-C(=O)-CH(OH)-Ph-X

However, the corresponding benzoin derivative for synthesizing the bis-dithiobenzilnickel complex of Formula [1] and/or [2] must have Substituent groups in only one of the two aromatic rings. Such a benzoin derivative is possible to be synthesized by using two types of benzaldehyde derivatives (benzaldehyde and a substituted benzaldehyde). However, in this method, a reaction between the same type of benzaldehyde derivative inevitably takes place, and thus has a problem in view of yield. In the present invention, the benzoin derivative is synthesized by a method using phenylglyoxal, in view of simplicity and yield of the reaction.

There are also provided according to the present invention, as a second embodiment, novel benzoin derivatives which are useful as intermediate in the syntheses of the bis-dithiobenzilnickel complexes of Formula [1] and/or [2]. These derivatives include the following compounds [3] to [20]:

4'-Ethylbenzoin [3]
4'-n-Propylbenzoin [4]
4'-iso-Propylbenzoin [5]
4'-n-Butylbenzoin [6]
4'-sec-Butylbenzoin [7]
4'-tert-Butylbenzoin [8]
4'-n-Amylbenzoin [9]
4'-n-Hexylbenzoin [10]
4'-n-Heptylbenzoin [11]
4'-n-Octylbenzoin [12]
2',5'-Dimethylbenzoin [13]
3',5'-Dimethylbenzoin [14]
3',4'-Dimethylbenzoin [15]
2',3',4',5'-Tetramethylbenzoin [16]
2',5'-Dimethoxybenzoin [17]
4'-Phenylbenzoin [18]
4'-Phenoxybenzoin [19]
4'-Cyclohexylbenzoin [20]

The compounds [3] to [20] can be synthesized by a method in which phenylglyoxal and a substituted benzene derivative are reacted in the presence of a Lewis acid. Specifically, phenylglyoxal and the substituted benzene derivative are dissolved in a halogenated hydrocarbon solvent such as dichloromethane or dichloroethane, a Lewis acid such as boron trifluoride etherate or titanium tetrachloride is added, and reacted at room temperature. The reaction mixture is extracted with ethylacetate, the extract is neutralized, washed, dried, and then evaporated. Then, the reaction product is recrystallized to yield the compounds [3] to [20].

The bis-dithiobenzilnickel complex of Formula [1] and or [2] was dissolved in a solvent, the solution was coated on paper, and the coated paper was measured for near-infrared absorption spectrum. As a result, the complex according to the present invention has a strong absorption in the near-infrared region, and the maximum absorption was 810 to 900 nm.

Bis-dithiobenzilnickel complex is also known to have superior characteristics as a quencher of singlet oxygen, and is used as a photo-discoloration prevention agent for cyanine dyes. The complex of the present invention is a near-infrared absorbing agent in itself, but may be combined with cyanine dyes or the like to obtain near-infrared absorbing materials.

There is further provided according to the present invention, as a third embodiment, an optical recording material using a bis-dithiobenzilnickel complex of Formula [1] and/or [2] or a near-infrared absorbing material comprising the complex.

Here, the optical recording material is a recording material provided on a substrate with a recording layer containing: (1) a near-infrared absorbent or a near-infrared absorbing material, (2) a coler developer and (3) a color former (metal salts of organic acids, metal salts of inorganic acids, or leuco dyes which react with the developer to develop a color).

The color developer and the color former used here can be conventional compounds known in the field of pressure sensitive and thermal recording paper.

The substrate used here can be paper, synthetic paper, laminated paper, non-woven fabrics, plastic sheets, pigment-filled plastic films, filler-coated plastic films, metal foils, or combinations thereof.

Bis-dithiobenzilnickel complex of Formula [1] and/or [2] was mixed with a sensitizer, and coated with a thermal color developing material on paper to obtain an optical recording material. When the recording material was irradiated with a laser light, it was found to provide a print of a high image density and a sufficient contrast. Furthermore, the complexes [21] to [42] provided improved brightness over conventional bis-dithiobenzilnickel.

The complexes of the present invention can also be applied to resins.

There is further provided according to the present invention, as a fourth embodiment, a near-infrared absorbing resin pellet comprising a bis-dithiobenzilnickel complex of Formula [1] and/or [2] or a near-infrared absorbing material comprising the complex, contained in a transparent resin, and a near-infrared absorbing resin molding obtained by molding the pellet.

The bis-dithiobenzilnickel complex of Formula [1] and/or [2] and the transparent resin pellet were kneaded by an extruder to form a near-infrared absorbing resin pellet. The pellet was then molded by a molding machine to form a near-infrared absorbing resin molding.

The transparent resin used here can be a substantially transparent resin with reduced absorption and scattering of visible light. Specifically, such resins include acrylic resins such as those of methacrylic esters, polystyrene, polyvinylchloride, polycarbonate, olefin resins, epoxy resins, and the like. Since the complex of the present invention is higher in decomposition temperature than the known near-infrared absorbing dyes in the prior art, it can be containe in resins which require higher temperatures for molding such as polycarbonate. The resins are used not only alone but also can be used as mixtures of two or more types.

In addition to the above method, the near-infrared absorbing resin molding can be produced by a method in which the bis-dithiobenzilnickel complex of Formula [1] and/or [2] or a near-infrared absorbing material comprising the complex is contained in a resin monomer, and the mixture is polymerized. For example, the bis-dithiobenzilnickel complex of Formula [1] and/or [2] is dissolved in methylmethacrylate monomer, and pre-polymerized using a polymerization initiator such as 2,2'-azobis-(isobutyronitrile), 2,2'-azobis-(2,4-dimethylvaleronitrile), or benzoylperoxide. The prepolymer is then poured into a mold for substantial polymerization to prepare a near-infrared absorbing resin molding.

The resulting resin molding has a characteristic absorption in the wavelength region 800–950 nm. The molding is useful for near-infrared cutting filters, semiconductor light receiving element filters, protective glasses for semiconductor lasers, and the like. Furthermore, the molding can also be applied to heat rays absorbing glazing materials and green house materials.

Furthermore, the complex of the present invention can also be contained in hard coating agents and ultraviolet curing resins.

The bis-dithiobenzilnickel complex of Formula [1] and/or [2] was dissolved in a hard coating agent, and the solution was applied to the surface of a substrate by coating or dipping, and heat cured to obtain a near-infrared absorbing material.

Here, the hard coating agent is a sol obtained by dissolving polysiloxane, which is a hydrolyzed product or partial condensation product of mainly a three-functional or four-functional organoalkoxysilane monomer by and acid or base, in a solvent such as alcohols, benzene, toluene, acetone, methylethylketone, methylcellosolve, or the like, and mixing with a hardener and various additives.

The substrate to which the hard coating agent is applied includes paper, tissue paper, synthetic paper, fibers, soft metals, natural or synthetic resins, or the like, in the form of films, sheets, boards, textiles, or any other specific shapes.

The bis-dithiobenzilnickel complex of Formula [1] and/or [2] was dissolved in an ultraviolet curing resin such as (meth)acrylic resins or (meth)alkoxysilane, filled in a space provided between two transparent glass plates, irradiated with ultraviolet rays through transparent glass to cure the ultraviolet curing resin, obtaining a near-infrared absorbing glass composite.

DESCRIPTION OF PREFERRED EMBODIMENTS

[EXAMPLE 1]

(4'-Ethylbenzoin [3]

Figure 1:
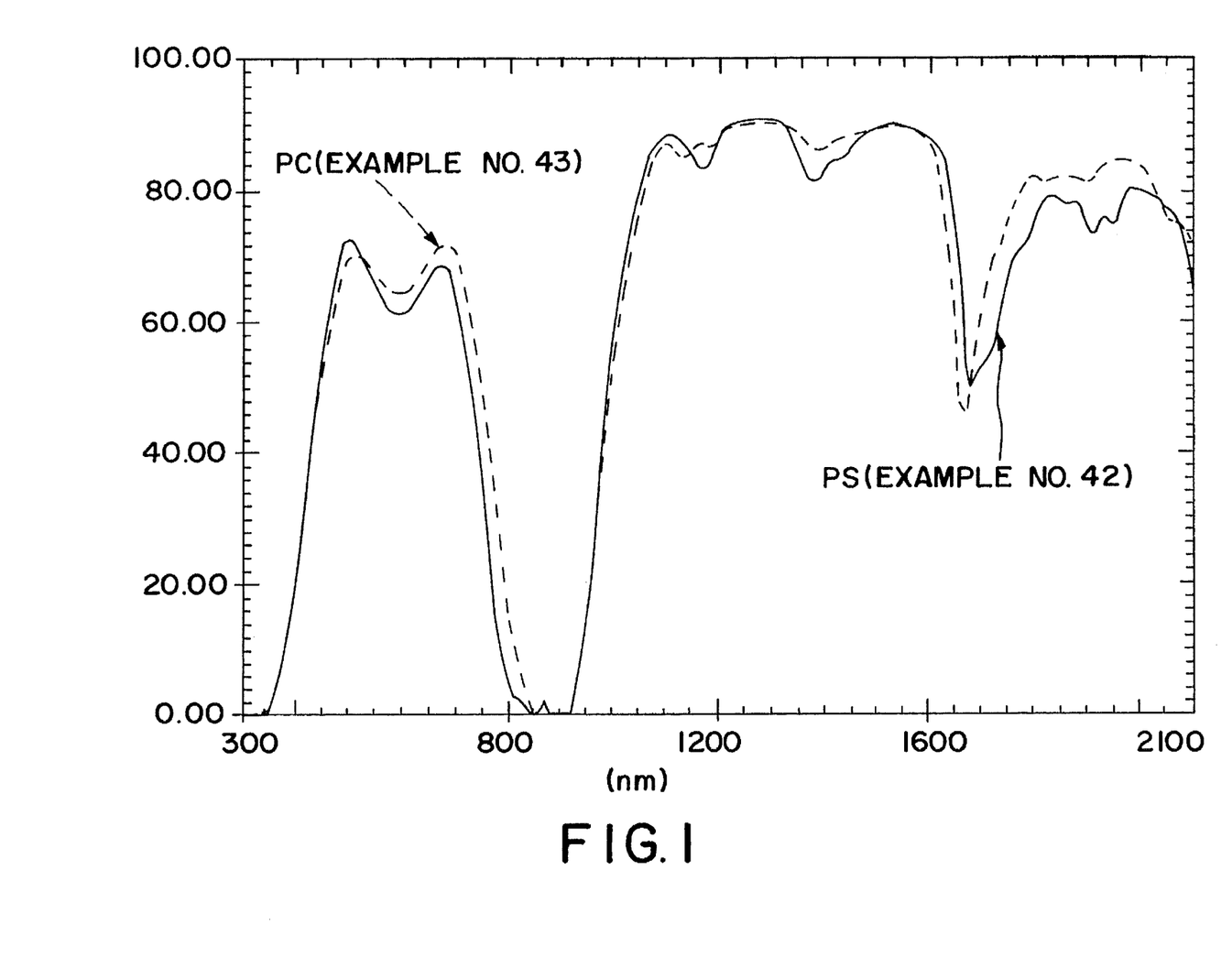
FIG. 1 is transmission spectra of a near-infrared absorbing resin molding obtained in Example 42 and in Example 43.

Phenylglyoxal monohydrate (304 mg, 2 mM) and ethylbenzene (0.49 ml, 4 mM) were dissolved in dichloroethane (4 ml), titanium tetrachloride (0.33 ml, 3 mM) was added, and reacted at room temperature for 2 hours. The reaction mixture was extracted with ethylacetate, the extract was washed with saturated sodium hydrogen carbonate solution and brine, dried with sodium sulfate anhydrous, and then concentrated to obtain a yellow-colored oil. The oil was crystallized from a petroleum ether/diethylether to obtain 357.1 mg (74.0% yield) of 4'-ethylbenzoin.

The product (benzoin compound) was identified by $^1$H-NMR. Basically, the production was confirmed by checking the peaks of the functional groups derived from phenylglyoxal and that from the substituted benzene, and the peak of α-hydrogen of the produced α-hydroxyketone (in the vicinity of δ=5.90). For 4'-ethylbenzoin, since peaks resulting from the aromatic ring of phenylglyoxal are noted at δ=7.39, 7.91), peaks from the aromatic ring of ethylbenzene at δ=7.12, 7.24, peaks from ethyl of ethylbenzene at δ=1.18, 2.58, and a peak from α-hydrogen of the α-hydroxyketone at δ=5.93, 4'-ethylbenzoin is identified. Also by IR spectrum, a peak of hydroxyl group of α-hydroxyketone is noted at 3417 cm$^{-1}$, and a peak of ketone is noted at 1676 cm$^{-1}$, indicating the structure of 4'-ethylbenzoin.

Melting point: 120°–121° C.

NMR (CDCl$_3$, δ): 1.18 (3H, t, J=7.5), 2.58 (2H, m), 4.50 (1H, broad d, J=3.0), 5.93 (1H, d, J=3.0), 7.12 (2H, d, J=7.5), 7.24 (2H, d, J=7.5), 7.39 (2H, tt, J=7.5, 1.5), 7.39 (1H, tt, J=7.5, 1.5), 7.91 (2H, dt, J=7.5, 1.5).

IR (ν, cm$^{-1}$): 3417, 1676.

[EXAMPLE 2]

(4'-n-Propylbenzoin [4])

Phenylglyoxal monohydrate (304 mg, 2 mM) and n-propylbenzene (0.56 ml, 4 mM) were dissolved in dichloroethane (6 ml), titanium tetrachloride (0.33 ml, 3 mM) was added, and reacted at room temperature for 2 hours. Using the same procedure as in Example 1, 4'-n-propylbenzoin was obtained as crystal (369.9 mg, 71.9% yield).

Melting point: 111°–112° C.

NMR (CDCl$_3$, δ): 4.52 (1H, d, J=5.0), 5.93 (1H, d, J=5.0), 7.12 (2H, d, J=7.5), 7.23 (2H, d, J=7.5), 7.37 (2H, tt, J=7.5, 1.5), 7.50 (1H, tt, J=7.5, 1.5), 7.91 (2H, dt, J=7.5, 1.5).

IR (ν, cm$^{-1}$): 3416, 1675.

[EXAMPLE 3]

(4'-iso-Propylbenzoin [5])

Phenylglyoxal monohydrate (304 mg, 2 mM) and cumene (0.56 ml, 4 mM) were dissolved in dichloroethane (4 ml), titanium tetrachloride (0.33 ml, 3 mM) was added, and reacted at room temperature for 4 hours. Using the same procedure as in Example 1, 4'-iso-propylbenzoin was obtained as crystal (300.6 mg, 59.6% yield).

Melting point: 116°–117° C.

NMR (CDCl$_3$, δ): 1.18 (3H, s), 1.20 (3H, s), 2.80 (1H, m), 5.93 (1H, s), 7.17 (2H, d, J=8.5), 7.25 (2H, d, J=8.5), 7.40 (2H, tt, J=7.0, 1.5), 7.52 (1H, tt, J=7.0, 1.5), 7.93 (2H, dt, J=7.0, 1.5).

IR (ν, cm$^{-1}$): 3415, 1678.

[EXAMPLE 4]

(4'-n-Butylbenzoin [6])

Phenylglyoxal monohydrate (304 mg, 2 mM) and n-butylbenzene (0.62 ml, 4 mM) were dissolved in dichloroethane (4 ml), titanium tetrachloride (0.33 ml, 3 mM) was added, and reacted at room temperature for 1 hour. Using the same procedure as in Example 1, 4'-n-butylbenzoin was obtained as crystal (362.7 mg, 67.2% yield).

Melting point: 75°–77° C.

NMR (CDCl$_3$, δ): 0.86–0.94 (3H, m), 1.22–1.38 (2H, m), 1.48–1.62 (2H, m), 2.52–2.64 (2H, m), 5.92 (1H, s), 7.13 (2H, d, J=8.0), 7.23 (2H, d, J=8.0), 7.39 (2H, tt, J=7.0, 1.5), 7.52 (1H, tt, J=7.0, 1.5), 7.92 (2H, dt, J=7.0, 1.5).

IR (ν, cm$^{-1}$): 3419, 1677.

[EXAMPLE 5]

(4'-sec-Butylbenzoin [7])

Phenylglyoxal monohydrate (304 mg, 2 mM) and sec-butylbenzene (0.62 ml, 4 mM) were dissolved in dichloroethane (4 ml), titanium tetrachloride (0.33 ml, 3 mM) was added, and reacted at room temperature for 2.5 hours. Using the same procedure as in Example 1, 4'-sec-butylbenzoin was obtained as crystal (200.6 mg, 37.3% yield).

Melting point: 77°–78° C.

NMR (CDCl$_3$, δ): 0.76 (3H, t, J=7.5), 1.17 (3H, m), 1.53 (1H, m), 2.54 (1H, m), 5.93 (1H, s), 7.13 (2H, d, J=8.0), 7.24 (2H, d, J=8.0), 7.40 (2H, tt, J=7.0, 1.5), 7.52 (1H, tt, J=7.0, 1.5), 7.93 (2H, dt, J=7.0, 1.5).

IR (ν, cm$^{-1}$): 3416, 1676.

[EXAMPLE 6]

(4'-tert-Butylbenzoin [8])

Phenylglyoxal monohydrate (304 mg, 2 mM) and tert-butylbenzene (0.62 ml, 4 mM) were dissolved in dichloroethane (2 ml), titanium tetrachloride (0.33 ml, 3 mM) was added, and reacted at room temperature for 2.5 hours. Using the same procedure as in Example 1, 4'-tert-butylbenzoin was obtained as crystal (216.9 mg, 40.5% yield).

Melting point: 114°–115° C.

NMR (CDCl$_3$, δ): 1.26 (9H, s), 5.94 (1H, s), 7.25 (2H, s), 7.25 (2H, dt, J=7.5, 1.5), 7.34 (2H, dt, J=7.5, 1.5), 7.40 (2H, tt, J=7.5, 1.5), 7.52 (1H, tt, J=7.5, 1.5), 7.94 (2H, dt, J=7.5, 1.5).

IR (ν, cm$^{-1}$): 3414, 1676.

[EXAMPLE 7]

(4'-n-Amylbenzoin [9])

Phenylglyoxal monohydrate (304 mg, 2 mM) and n-amylbenzene (0.69 ml, 4 mM) were dissolved in dichloroethane (3 ml), titanium tetrachloride (0.33 ml, 3 mM) was added, and reacted at room temperature for 2 hours. Using the same procedure as in Example 1, 297.1 mg (52.6% yield) of 4'-n-amylbenzoin was obtained as crystal (297.1 mg, 52.6% yield).

Melting point: 83°–84° C.

NMR (CDCl$_3$, δ): 0.88(3H, t, J=6.5), 1.20–1.35 (4H, m), 1.48–1.62 (2H, m), 2.53 (2H, dd, J=8.0, 7.0), 5.92 (1H, s), 7.13 (2H, d, J=8.0), 7.23 (2H, d, J=8.0), 7.38 (2H, tt, J=7.5, 1.5), 7.51 (1H, tt, J=7.5, 1.5), 7.92 (2H, dt, J=7.5, 1.5).

IR (ν, cm$^{-1}$): 3417, 1676.

[EXAMPLE 8]

(4'-n-Hexylbenzoin [10])

Phenylglyoxal monohydrate (304 mg, 2 mM) and n-hexylbenzene (0.76 ml, 4 mM) were dissolved in dichloroethane (3 ml), titanium tetrachloride (0.33 ml, 3 mM) was added, and reacted at room temperature for 1 hour. Using the same procedure as in Example 1, 4'-n-hexylbenzoin was obtained as crystal (352.8 mg, 59.4% yield).

Melting point: 87°–88° C.

NMR (CDCl$_3$, δ): 0.85 (3H, t, J=7.0), 1.20–1.32 (6H, m), 1.48–1.64 (2H, m), 2.53 (2H, t, J=7.5), 4.50 (1H, d, J=5.0), 5.92 (1H, d, J=5.0), 7.12 (2H, d, J=8.0), 7.23 (2H, d, J=8.0), 7.40 (2H, tt, J=7.5, 1.5), 7.52 (1H, tt, J=7.5, 1.5), 7.92 (2H, dt, J=7.5, 1.5).

IR (ν, cm$^{-1}$): 3414, 1678.

[EXAMPLE 9]

(4'-n-Heptylbenzoin [11])

Phenylglyoxal monohydrate (304 mg, 2 mM) and n-heptylbenzene (0.82 ml, 4 mM) were dissolved in dichloroethane (3 ml), titanium tetrachloride (0.33 ml, 3 mM) was added, and reacted at room temperature for 1 hour. Using the same procedure as in Example 1, 4'-n-heptylbenzoin was obtained as crystal (386.7 mg, 61.5% yield).

Melting point: 82°–83° C. NMR (CDCl$_3$, δ): 0.86 (3H, t, J=7.0), 1.18–1.32(8H, m), 1.48–1.60 (2H, m), 2.54 (2H, dd, J=8.0, 7.5), 5.92 (1H, s), 7.13 (2H, d, J=8.0), 7.23 (2H, d, J=8.0), 7.39 (2H, tt, J=7.5, 1.5), 7.52 (1H, tt, J=7.5, 1.5), 7.92 (2H, dt, J=7.5).

IR (ν, cm$^{-1}$): 3416, 1677.

[EXAMPLE 10]

(4'-n-Octylbenzoin [12])

Phenylglyoxal monohydrate (608 mg, 4 mM) and n-octylbenzene (1.77 ml, 8 mM) were dissolved in dichloroethane (8 ml), titanium tetrachloride (0.66 ml, 6 mM) was added, and reacted at room temperature for 30 minutes. Using the same procedure as in Example 1, 4'-n-octylbenzoin was obtained as crystal (810.0 mg, 62.6% yield).

Melting point: 88°–89° C.

NMR (CDCl$_3$, δ): 0.86 (3H, t, J=7.5), 1.20–1.32 (10H, m), 1.48–1.60 (2H, m), 2.54 (2H, dd, J=8.0, 7.5), 5.92 (1H, s), 7.12 (2H, d, J=8.0), 7.23 (2H, d, J=8.0), 7.38 (2H, tt, J=7.5, 1.5), 7.52 (1H, tt, J=7.5, 1.5), 7.92 (2H, dt, J=7.5, 1.5).

IR (ν, cm$^{-1}$): 3414, 1679.

[EXAMPLE 11]

(2',5'-Dimethylbenzoin [13])

Phenylglyoxal monohydrate (500 mg, 3.29 mM) and p-xylene (0.56 ml, 4.79 mM) were dissolved in dichloroethane (5 ml), titanium tetrachloride (0.9 ml, 8.2 mM) was added, and reacted at room temperature for 30 minutes. Using the same procedure as in Example 1, 2',5'-dimethylbenzoin was obtained as crystal (587.7 mg, 73.9% yield).

Melting point: 91°–93° C.

NMR (CDCl$_3$, δ): 2.18 (3H, s), 2.49 (3H, s), 4.54 (1H, broad s), 6.01 (1H, s), 6.82 (1H, broad s), 6.98 (1H, broad d, J=8.0), 7.09 (1H, d, J=8.0), 7.36 (2H, tt, J=7.5, 1.5), 7.49 (1H, tt, J=7.5, 1.5), 7.81 (2H, dt, J=7.5, 1.5).

IR (ν, cm$^{-1}$): 3472, 1671.

[EXAMPLE 12]

(3',5'Dimethylbenzoin [14])

Phenylglyoxal monohydrate (304 mg, 2 mM) and m-xylene (0.49 ml, 4 mM) were dissolved in dichloroethane (4 ml), titanium tetrachloride (0.33 ml, 3 mM) was added, and reacted at room temperature for 30 minutes. Using the same procedure as in Example 1, 3', 5'-dimethylbenzoin was obtained as a light-yellow oil (363.2 mg, 75.3% yield).

NMR (CDCl$_3$, δ): 2.25 (3H, s), 2.50 (3H, s), 4.34 (1H, s), 6.01 (1H, s), 6.90 (2H, s), 7.02 (1H, s), 7.36 (2H, tt, J=7.5, 1.5), 7.49 (1H, tt, J=7.0, 1.5), 7.82 (2H, dt, J=7.0, 1.5).

IR (ν, cm$^{-1}$): 3456, 1682.

[EXAMPLE 13]

(3',4'-Dimethylbenzoin [15])

Phenylglyoxal monohydrate (304 mg, 2 mM) and o-xylene (0.49 ml, 4 mM) were dissolved in dichloroethane (4 ml), titanium tetrachloride (0.33 ml, 3 mM) was added, and reacted at room temperature for 20 minutes. Using the same procedure as in Example 1, 3',4'-dimethylbenzoin was obtained as crystal (258.7 mg, 54.0% yield).

Melting point: 127°–129° C.

NMR (CDCl$_3$, δ): 2.19 (3H, s), 2.20 (3H, s), 4.47 (1H, d, J=6.2), 5.89 (1H, d, J=6.2), 7.08–7.09 (3H, m), 7.39 (2H, tt, J=7.0, 1.5), 7.51 (1H, tt, J=7.0, 1.5), 7.93 (2H, dt, J=7.0, 1.5).
IR (ν, cm$^{-1}$): 3456, 1673.

[EXAMPLE 14]

(2',3',4',5'-Tetramethylbenzoin [16])

Phenylglyoxal monohydrate (304 mg, 2 mM) and 1,2,3,4-tetramethylbenzene (0.60 ml, 4 mM were dissolved in dichloroethane (5 ml), titanium tetrachloride (0.33 ml, 3 mM) was added, and reacted at room temperature for 10 minutes. Using the same procedure as in Example 1, 2',3',4',5'-tetramethylbenzoin was obtained (378.2 mg, 70.7% yield).
Melting point: 99°–101° C.
NMR (CDCl$_3$, δ): 2.12 (3H, s), 2.13 (3H, s), 2.22 (3H, s), 2.44 (3H, s), 4.31 (1H, broad s), 6.07 (1H, s), 6.64 (1H, s), 7.35 (2H, tt, J=7.0, 1.5), 7.48 (1H, tt, J=7.0, 1.5), 7.83 (2H, dt, J=7.0, 1.5).
IR (ν, cm$^{-1}$): 3468, 1665.

[EXAMPLE 15]

(2',5'-Dimethoxybenzoin [17])

Phenylglyoxal monohydrate (152 mg, 1 mM) and p-dimethoxybenzene (0.21 ml, 1.5 mM) were dissolved in dichloroethane (2 ml), titanium tetrachloride (0.33 ml, 3 mM) was added, and reacted at room temperature for 4 hours. Using the same procedure as in Example 1, 2',5'-dimethoxylbenzoin was obtained as an oil (219.4 mg, 79.2% yield).
NMR (CDCl$_3$, δ): 3.69 (3H, s), 3.82 (3H, s), 4.53 (1H, broad s), 6.23 (1H, s), 6.77 (1H, d, J=8.5), 6.82 (1H, d, J=8.5), 7.36 (2H, tt, J=7.5, 1.5), 7.50 (1H, tt, J=7.5, 1.5), 7.94 (2H, dt, J=7.5, 1.5).
IR (ν, cm$^{-1}$): 3456, 1683.

[EXAMPLE 16]

(4'-Phenylbenzoin [18])

Phenylglyoxal monohydrate (200 mg, 1.31 mM) and diphenyl (405 mg, 2.62 mM) were dissolved in dichloroethane (5 ml), titanium tetrachloride (0.15 ml, 1.31 mM) was added, and reacted at room temperature for 20 minutes. Using the same procedure as in Example 1, 4'-phenylbenzoin was obtained as crystal (136.0 mg, 35.5% yield).
Melting point: 150°–151° C.
NMR (CDCl$_3$, δ): 6.01 (1H, s), 7.33 (2H, tt, J=7.0, 1.5), 7.38–7.46 (5H, m), 7.51–7.57 (5H, s), 7.96 (2H, dt, J=7.0, 1.5).
IR (ν, cm$^{-1}$): 3426, 1679.

[EXAMPLE 17]

(4'-Phenoxybenzoin [19])

Phenyglyoxal monohydrate (200 mg, 1.31 mM) and diphenylether (0.4 ml, 2.62 mM) were dissolved in dichloroethane (3 ml), titanium tetrachloride (0.07 ml, 0.66 mM) was added, and reacted at room temperature for 1 hour. Using the same procedure as in Example 1, 4'-phenoxybenzoin was obtained as crystal (331.2 mg, 80.7% yield).
Melting point 100°–102° C.
NMR (CDCl$_3$, δ): 5.94 (1H, s), 6.92 (2H, dd, J=7.5, 1.0), 6.97 (2H, dd, J=7.5, 1.0), 7.10 (1H, ddd, J=7.5, 6.5, 1.0), 7.27 (2H, t, J=6.5), 7.29 (2H, d, J=6.5), 7.31 (2H, tt, J=7.5, 1.5), 7.40 (1H, tt, J=7.0, 1.5), 7.92 (2H, dt, J=7.0, 1.5).
IR (ν, cm$^{-1}$): 3422, 1674.

[EXAMPLE 18]

(4'-Cyclohexylbenzoin [20])

Phenylglyoxal monohydrate (304 mg, 2 mM) and phenylcyclohexyl (0.67 ml, 4 mM) were dissolved in dichloroethane (4 ml), titanium tetrachloride (0.33 ml, 3 mM) was added, and reacted at room temperature for 1.5 hours. Using the same procedure as in Example 1, 4'-cyclohexylbenzoin was obtained as crystal (441.8 mg, 75.2% yield).
Melting point: 139°–140° C.
NMR (CDCl$_3$, δ): 1.14–1.44 (5H, m), 1.66–1.68 (6H, m), 4.48 (1H, d, J=6.0), 5.93 (1H, d, J=6.0), 7.13 (2H, dd, J=7.0, 1.5 ), 7.24 (2H, dd, J=7.0, 1.5), 7.40 (2H, tt, J=7.5, 1.5), 7.52 (1H, tt, J=7.5, 1.5), 7.93 (2H, dt, J=7.5, 1.5).
IR (ν, cm$^{-1}$): 3414, 1677.

[EXAMPLES 19–36]

Each of the benzoin compounds (1 equivalent) synthesized in Examples 1–18 was dissolved in 1,4-dioxane, phosphorus pentasulfide (3 equivalents) was added, and reacted for 2 hours under reflux. The reaction mixture was filtered, the filtrate was mixed with an aqueous solution of nickel chloride hexahydrate (0.5 equivalent), and refluxed further for 2hours. The resulting reaction precipitate was filtered, which was extracted with methylene chloride and purified to give an objective bis-dithiobenzilnickel complex.

[EXAMPLES 37–40]

Using 4'-methylbenzoin, 2', 4', 6'-trimethylbenzoin, 4'-methoxybenzoin, and 4'-chlorobenzoin as materials, each was reacted by the same method as shown in Examples 19–36 to give a corresponding bis-dithiobenzilnickel complex.

The complexes obtained in Examples 19–40 were identified by IR spectrum and X-ray microanalysis. Further, the resulting complex was dissolved in methylene chloride, dropped onto Whatman filter paper, dried, and measured for near-infrared absorption spectrum by means of the Nippon Bunko UNIDEC-590 Near-Infrared Recording Spectrophotometer.

Bis-(4-methyldithiobenzil)-nickel [21]
 Yield: 12.2%
 IR (ν, cm$^{-1}$): 1356, 1140, 884, 755, 695
 X-ray microanalysis: S/Ni=4.09
 Maximum absorptions: 840–850 nm
Bis-(4-ethyldithiobenzil)-nickel [22]
 Yield: 13.4%
 IR (ν, cm$^{-1}$): 2950, 2864, 2864, 1358, 1140, 883, 755, 695
 X-ray microanalysis: S/Ni=4.38
 Maximum absorptions: 825–835 nm
Bis-(4-n-propyldithiobenzil)-nickel [23]
 Yield: 6.7%
 IR (ν, cm$^{-1}$): 2954, 2859, 1357, 1140, 883, 754, 692
 X-ray microanalysis: S/Ni=4.39
 Maximum absorptions: 825–835 nm
Bis-(4-iso-propyldithiobenzil)-nickel [24]
 Yield : 11.4%
 IR (ν, cm$^{-1}$): 2956, 2864, 1359, 1142, 884, 756, 693
 X-ray microanalysis: S/Ni=4.12
 Maximum absorptions: 860–880 nm
Bis-(4-n-butyldithiobenzil)-nickel [25]
 Yield: 28.5%
 IR (ν, cm$^{-1}$): 2951, 2856, 1359, 1141, 884, 753, 694
 X-ray microanalysis: S/Ni=4.39
 Maximum absorptions: 830–845 nm
Bis-(4-sec-butyldithiobenzil)-nickel [26]

Yield: 5.9%
IR (v, cm$^{-1}$): 2958, 2864, 1358, 1140, 883, 754, 693
X-ray microanalysis: S/Ni=4.39
Maximum absorptions: 870–880 nm
Bis-(4-tert-butyldithiobenzil)-nickel [27]
Yield: 5.1%
IR (v, cm$^{-1}$): 2957, 2862, 1356, 1141, 884, 755, 693
X-ray microanalysis: S/Ni=4.24
Maximum absorptions: 870–880 nm
Bis-(4-n-amyldithiobenzil)-nickel [28]
Yield: 13.8%
IR (v, cm$^{-1}$): 2922, 2855, 1359, 1141, 884, 754, 694
X-ray microanalysis: S/Ni=4.18
Maximum absorptions: 875–855 nm
Bis-(4-n-hexyldithiobenzil)-nickel [29]
Yield: 13.5%
IR (v, cm$^{-1}$): 2920, 2851, 1358, 1140, 883, 752, 692
X-ray microanalysis: S/Ni=4.09
Maximum absorptions: 875–885 nm
Bis-(4-n-heptyldithiobenzil)-nickel [30]
Yield: 12.1%
IR (v, cm$^{-1}$): 2921, 2852, 1360, 1142, 885, 753, 694
X-ray microanalysis: S/Ni=4.35
Maximum absorptions: 870–880 nm
Bis-(4-n-octyldithiobenzil)-nickel [31]
Yield: 11.4%
IR (v, cm$^{-1}$): 2922, 2851, 1359, 1141, 884, 751, 692
X-ray microanalysis: S/Ni=4.27
Maximum absorptions: 850–860 nm
Bis-(2,5-dimethyldithiobenzil)-nickel [32]
Yield: 14.3%
IR (v, cm$^{-1}$): 1363, 1147, 1114, 856, 754, 692
X-ray microanalysis: S/Ni=4.06
Maximum absorptions: 825–835 nm
Bis-(3,5-dimethyldithiobenzil)-nickel [33]
Yield: 3.3%
IR (v, cm$^{-1}$): 1357, 1142, 1029, 867, 7575, 686
X-ray microanalysis: S/Ni=4.03
Maximum absorptions: 850–860 nm
Bis-(3,4-dimethyldithiobenzil)-nickel [34]
Yield: 13.5%
IR (v, cm$^{-1}$): 1343, 1140, 1021, 860, 751, 695
X-ray microanalysis: S/Ni=4.07
Maximum absorptions: 880–890 nm
Bis-(2,4,6-trimethyldithiobenzil)-nickel [35]
Yield: 3.2%
IR (v, cm$^{-1}$): 1345, 870, 754, 695
X-ray microanalysis: S/Ni=4.16
Maximum absorptions: 870–880 nm
Bis-(2,3,4,5-tetramethyldithiobenzil)-nickel [36]
Yield: 11.2%
IR (v, cm$^{-1}$): 2866, 1362, 1190, 880, 759, 694
X-ray microanalysis: S/Ni=4.02
Maximum absorptions: 850–860 nm
Bis-(4-methoxydithiobenzil)-nickel [37]
Yield: 1.1%
IR (v, cm$^{-1}$): 1360, 1220, 752, 693
X-ray microanalysis: S/Ni=4.36
Maximum absorptions: 850–860 nm
Bis-(2,5-dimethoxydithiobenzil)-nickel [38]
Yield: 18.6%
IR (v, cm$^{-1}$): 2929, 1361, 1221, 1113, 939, 760, 696
X-ray microanalysis: S/Ni=4.26
Maximum absorptions: 870–880 nm
Bis-(4-phenyldithiobenzil)-nickel [39]
Yield: 5.7%
IR (v, cm$^{-1}$): 1477, 1357, 1138, 879, 757, 693
X-ray microanalysis: S/Ni=4.49
Maximum absorptions: 830–840 nm
Bis-(4-phenoxydithiobenzil)-nickel [40]
Yield: 22.1%
IR (v, cm$^{-1}$): 1486, 1358, 1236, 1137, 868, 750, 692
X-ray microanalysis: S/Ni=4.28
Maximum absorptions: 835–845 nm
Bis-(4-cyclohexyldithiobenzil)-nickel [41]
Yield: 17.6%
IR (v, cm$^{-1}$): 2919, 2848, 1357, 1140, 885, 754, 693
X-ray microanalysis: S/Ni=4.42
Maximum absorptions: 845–855 nm
Bis-(4-chlorodithiobenzil)-nickel [42]
Yield: 5.6%
IR (v, cm$^{-1}$): 1357, 1140, 1093, 884, 755, 695
X-ray microanalysis: S/Ni=3.96
Maximum absorptions: 865–875 nm

[EXAMPLE 41]

An electron donating colorless dye dispersion (solution A), an electron accepting acid dispersion (solution B), and a light absorbing sensitizer dispersion (solution C) containing bis-(4-ethyldithiobenzil)-nickel of the following compositions were individually wet milled by a sand grinder. Then, 7.3 parts of the solution A, 30 parts of the solution B, 20 parts of the solution C, 25 parts of 25% aqueous silica dispersion, and 10% aqueous PVA solution were mixed to obtain a coating color. The coating color was coated to a coverage of 5 g/m$^2$ on fine paper with a substance of 60 g/m$^2$ using a Meyer bar, and dried to give an optical recording material.

| Solution A: Electron donating colorless dye dispersion | |
|---|---|
| ODB | 2.0 parts |
| 10% Aqueous PVA solution | 3.4 |
| Water | 1.9 |
| Solution B: Electron accepting acid dispersion | |
| Bisphenol A | 6.0 parts |
| 10% Aqueous PVA solution | 15.0 |
| Water | 9.0 |
| Solution C: Light absorbing sensitizer dispersion | |
| 49 Parts of p-benzylbiphenyl (PBB) was mixed with 1 part of bis-(4-ethyldithiobenzil)-nickel, and melted by heating to 100–150° C. The mixture was milled by a sand grinder to obtain a light absorbing sensitizer. | |
| Light absorbing sensitizer | 4.0 parts |
| 10% Aqueous PVA solution | 10.0 |
| Water | 6.0 |

*ODB: 3-diethylamino-6-methyl-7-anilinofluorane

The thus prepared optical recording material was irradiated with laser light by a device comprising a semiconductor laser head combined with a focusing lens to obtain a print.

The optical recording material was measured for reflectance by the Toyo Seiki TYPE-D Hunter Reflectometer, and showed a reflectance of 73.01%.

[Comparative Example 1]

Dithiobenzilnickel complexes, which are known in the prior art were individually dissolved in methylene chloride, dropped onto a Whatman filter paper, dried, and measured for near-infrared absorption spectrum as in the above Example 19–41.

| | |
|---|---|
| Bis-(dithiobenzil)-nickel | |
| Maximum absorptions: | 850–890 nm |
| Bis-4,4'-dimethyldithiobenzil)-nickel | |
| Maximum absorptions: | 875–890 nm |
| Bis-(4-dimethylaminodithiobenzil)-nickel | |
| Maximum absorptions: | 1060–1070 nm |
| Bis-(4-diethylaminodithiobenzil)-nickel | |
| Maximum absorptions: | 1100–1120 nm |

[Comparative Example 2]

Using bis-(dithiobenzil)-nickel, an optical recording material was prepared by the same method as used in Example 41. The optical recording material had a reflectance of 71.88%.

[EXAMPLE 42]

Bis-(4-ethyldithiobenzil)-nickel (0.05 parts) and polystyrene pellet (tradename: Estyrene (Nippon Steel Chemical) 99.95 parts) were mixed, and extruded by an extruder to produce a pellet containing bis-dithiobenzil-nickel complex. The resulting pellet was molded by a molding machine to obtain a 2.0 mm thick resin plate.

[EXAMPLE 43]

Bis-(4-ethyldithiobenzil)-nickel (0.05 parts) and polycarbonate pellet (tradename: Toughlon (Idemitsu Petrochemical) 99.95 parts) were mixed, and extruded by an extruder to produce a pellet containing bis-dithiobenzil-nickel complex. The resulting pellet was molded by a molding machine to obtain a 2.0 mm thick resin plate.

[EXAMPLE 44]

Bis-(4-ethyldithiobenzil)-nickel (0.02 parts) was dissolved in methylmethacrylate monomer (99.98 parts). This solution was mixed with 2,2'-azobis-isobutyronitrile (1 part) and treated at 70° C. for 1 hour. The resulting syrup was poured into a mold comprising two glass plates by a conventional method known in the prior art, treated at 70° C. for 3 hours, followed by treatment at 100° C. for 1 hour, cooled, and released from the mold to obtain a 2.6 mm thick resin plate.

[EXAMPLE 45]

Bis-(4-n-propyldithiobenzil)-nickel (0.01 part) was dissolved in a silicone hard coating agent (tradename: Si-801A (Daihachi Kagaku) (200 parts)) to prepare a near-infrared absorbing hard coating composition. The composition was coated on a polyester film (tradename: AK Clear Film (Kimoto)) using a Meyer bar, air-dried, and heated in an oven at 150° C. for 2 minutes to obtain a near-infrared absorbing film.

[EXAMPLE 46]

Bis-(4-ethyldithiobenzil)-nickel (0.01 part) was dissolved in an ultraviolet curing resin (tradename: UVEKOL-S20 (UCB) (200 parts)) to prepare a near-infrared absorbing intermediate layer solution for glass composite, the intermediate layer solution was injected between two glass plates incorporated in a 1.5 mm thick spacer, cured by irradiating with a 400-W mercury lamp to obtain a glass composite.

The complexes according to the present invention, for example, bis-(4-ethyldithiobenzil)-nickel, bis-(4-n-propyldithiobenzil)-nickel, and bis-(3,5-dimethyldithiobenzil)-nickel of the present invention have maximum absorptions in the vicinity of 830 nm in a paper-coated state, and are thus superior as sensing materials to the semiconductor laser (830 nm) over the known materials. Furthermore, the complexes are also superior in brightness to the known materials, and are thus very promising for use as near-infrared absorbents or near-infrared absorbing materials for optical recording materials.

Furthermore, the complexes of the present invention can be used in near-infrared absorbing resin moldings by containing in a transparent resin, near-infrared absorbing materials provided with a near-infrared absorbing hard coating layer by containing in a hard coating agent, or in near-infrared absorbing glass composites by containing in an ultraviolet curing resin. These near-infrared absorbing materials have characteristic absorptions in 800–950 nm, and can thus be applied, in addition to optical recording media, to near-infrared cutting filters, light receiving element filters, protective eyeglasses for semiconductor lasers, goggles, heat rays shielding eyeglasses, sunglasses, heat rays shielding films, agricultural films, green house materials, optical disks, and the like. The complexes are also effective as antioxidants, weather resistant agents, and discoloration-prevention agents for dyes since they are superior as singlet oxygen quenchers.

We claim:

1. An optical recording material having, on a substrate, a recording layer comprising (a) an electron-donating colorless dye, (b) an electron-accepting acid compound which will react with said dye under heating to develop a color, and (c) a near-infrared absorbing material selected from the group consisting of the following bis-dithiobenzilnickel complexes capable of converting infrared light to heat:

-continued and

-continued

2. The optical recording material of claim 1, wherein said recording layer further comprises (d) a sensitizer.

3. The optical recording material of claim 2, wherein said sensitizer (d) is dispersed with said near-infrared absorbing material (c) to include therein said near-infrared absorbing material, followed by pulverization.

4. The optical recording medium of claim 1 wherein the near-infrared absorbing material is the bis-dithiobenzilnickel complex of the formula

5. The optical recording medium of claim 1 wherein the near-infrared absorbing material is the bi-dithiobenzilnickel complex of the formula

6. The optical recording medium of claim 1 wherein the near-infrared absorbing material is the bi-dithiobenzilnickel complex of the formula

7. The optical recording medium of claim 1 wherein the near-infrared absorbing material is the bi-dithiobenzilnickel complex of the formula

8. The optical recording medium of claim 1 wherein the near-infrared absorbing material is the bis-dithiobenzilnickel complex of the formula

9. The optical recording medium of claim 1 wherein the near-infrared absorbing material is the bis-dithiobenzilnickel complex of the formula

* * * * *